United States Patent [19]

Kimura et al.

[11] Patent Number: 4,464,400

[45] Date of Patent: Aug. 7, 1984

[54] SKIN CARE BASE MATERIAL FOR EXTERNAL USE

[75] Inventors: Kuniko Kimura, Tokyo; Kunihiko Ofuchi; Koichiro Oda, both of Yokohama, all of Japan

[73] Assignee: Mitsubishi Chemical Industries Limited, Tokyo, Japan

[21] Appl. No.: 358,588

[22] Filed: Mar. 16, 1982

[30] Foreign Application Priority Data

Apr. 8, 1981 [JP] Japan .................................. 56-52732

[51] Int. Cl.³ ........................ A61K 7/46; A61K 47/00
[52] U.S. Cl. ................................ 424/365; 252/522 R; 424/70; 424/273 R; 424/284; 424/322; 424/359; 424/362; 424/366
[58] Field of Search .................. 424/68, DIG. 5, 365, 424/358

[56] References Cited

U.S. PATENT DOCUMENTS

| | | | |
|---|---|---|---|
| 3,386,835 | 6/1968 | Schaap | 424/602 |
| 3,917,859 | 11/1975 | Terada et al. | 424/602 |
| 4,097,403 | 6/1978 | Tsutsumi et al. | 424/59 |

FOREIGN PATENT DOCUMENTS 884688  12/1961  United Kingdom ................ 424/365

OTHER PUBLICATIONS

Spalton, Pharmaceutical Emulsions & Emulsifying Agents, 8/1950, pp. 28, 29, 69, 70, 71, 73, 92, 93, 94, 95, 114, 115, 121, 117.

Sagarin, Cosmetics Science & Technology, 1957, pp. 149 to 179.

*Primary Examiner*—Dale R. Ore
*Attorney, Agent, or Firm*—Oblon, Fisher, Spivak, McClelland & Maier

[57] ABSTRACT

A skin care base material for external use comprising a phospholipid, an ester of a fatty acid and a polyoxyethylene fatty acid ester is disclosed.

10 Claims, No Drawings

SKIN CARE BASE MATERIAL FOR EXTERNAL USE

BACKGROUND OF THE INVENTION

1. Field of the Invention

The present invention relates to a skin care base material for external use, and more particularly to a skin care base material for external use containing a phospholipid.

2. Description of the Prior Art

A phospholipid such as lecithin is contained in a sebum component, and therefore believed to be suitable as a starting material of a skin care base material for external use such as a cosmetic for skin care. However, when used as a material for a cosmetic, the phospholipid has difficulties in the thermal and storage stability, and accordingly, it has not very much been utilized.

SUMMARY OF THE INVENTION

It has now been found that a skin care base material for external use which has an adequate stability and which gives a good feeling, when applied to the skin can be obtained by combining the phospholipid with an ester of a fatty acid and an ester of a polyoxyethylene fatty acid.

Namely, the present invention provides a skin care base material for external use which comprises a phospholipid, an ester of a fatty acid, and a polyoxyethylene fatty acid ester.

DESCRIPTION OF THE PREFERRED EMBODIMENTS

Firstly, as the phospholipid to be incorporated in the base material of the present invention, there may be mentioned, for instance, phosphatidylcholine (i.e. lecithin), phosphatidylethanolamine (i.e. cephalin), phosphatidylserine, phosphatidylinositol and phosphatidic acid. Although these may be used as a mixture of two or more different kinds, it is most preferred that the content of phosphatidylcholine in the phospholipid is within a range of from 10 to 40%.

For the practical purposes, it is advantageous to use a soybean phospholipid or an egg phospholipid, as the phospholipid. The amount of the phospholipid to be used, may vary depending upon the kind of the intended base material. However, the amount is usually from 0.05 to 20% by weight, preferably from 0.2 to 6% by weight, based on the weight of the entire composition.

As the ester of a fatty acid to be used together with the above mentioned phospholipid in the present invention, there may be mentioned a primary higher alcohol ester of a higher fatty acid. As the fatty acid, there may be mentioned the one having from 8 to 26 carbon atoms, preferably from 12 to 18 carbon atoms. If the carbon atoms are less than 8, such a fatty acid tends to give irritation to the skin. On the other hand, if the carbon atoms are more than 26, such a fatty acid is not preferred because of its poor feeling when applied to the skin.

Namely, as the fatty acid, there may be mentioned, for instance, a saturated fatty acids such as lauric acid, tridecylic acid, myristic acid or palmitic acid, or an unsaturated fatty acid such as oleic acid. Whereas, as the above mentioned alcohol, there may be mentioned, the one having from 8 to 22 carbon atoms, such as dodecyl alcohol, myristyl alcohol, stearyl alcohol, octyldodecyl alcohol, hexadecyl alcohol, or cetyl alcohol. Among them, the branched alcohols are preferred to the straight chained alcohols, since they have a low solidifying point and a high boiling point and thus are stable in the air. As such branched alcohols, there may be mentioned, for instance, hexadecyl alcohol or octyldodecyl alcohol.

Namely, as the ester of a fatty acid, octyldodecyl myristate, octyldodecyl oleate or hexyldecyl dimethyloctanoate is preferably used.

Next, the polyoxyethylene fatty acid ester to be used in the present invention, is usually a monoester, and the fatty acid component thereof is selected from those having from 8 to 26 carbon atoms, preferably from 12 to 18 carbon atoms. For instance, there may be mentioned lauric acid, palmitic acid, stearic acid, or oleic acid. And, those containing from 20 to 60 moles, preferably from 40 to 55 moles, of the ethylene oxide unit are preferably used. As the polyoxyethylene fatty acid ester, polyoxyethylene monooleate or polyoxyethylene monostearate, is preferably used.

The amount of use of the ester of a fatty acid is usually within a range of from 0.02 to 10% by weight, based on the weight of the entire composition. The polyoxyethylene fatty acid ester is used in an amount of from 0.01 to 5% by weight.

The skin care base material and a cosmetic carrier for external use according to the present invention contains the above mentioned three components including the phospholipid. However, depending upon the particular purpose, there may be added various other components in accordance with the common practice, for instance, to obtain an aqueous mixture, such as a solution, a colloidal solution, an emulsified lotion, an O/W cream (i.e. a hydrophilic cream) or an aqueous gel, where the aqueous phase constitutes a continuous phase, or an oil mixture such as a W/O cream or solution. As such components, there may be used those which are commonly used for cosmetics or medicines for external use, such as an oil-and-fat component, an emulsifier, a dispersant, a gelating agent, a chelating agent, a perfume, a vitamin, an anti-inflammatory agent such as allantoin and a moisture maintaining agent such as urea.

The skin care base material for external use according to the present invention, is suitable for use in the production of e.g. cosmetics such as various creams, lotions, shampoos or soaps, or medicines for external use such as ointments or creams, and it is superior in its thermal and storage stability without a trouble of colour change. Thus, it provides a skin care agent for external use which gives a good feeling when applied to the skin.

Now, the present invention will be described in further detail with reference to Examples. However, the present invention is not limited to these examples, and covers any other modifications unless they are beyond the gist of the present invention.

EXAMPLE 1 (SKIN CREAM)

| | | |
|---|---|---|
| (A) | Soybean phospholipid | 2.0% by weight |
| | 2-Octyldodecyl myristate | 1.5 |
| | Polyoxyethylene (40) monostearate | 1.8 |
| | Stearyl alcohol | 1.5 |
| | Cetyl alcohol | 4.0 |
| | Squalane | 4.0 |
| | Butyl p-hydroxybenzoate | 0.1 |
| | Dibutylhydroxytoluene | 0.05 |
| (B) | 1,3-Butylene glycol | 5.0 |
| | Methyl p-hydroxybenzoate | 0.1 |
| | Potassium hydroxide solution (10%) | 3 |
| | Sodium laurylsulfate | 0.1 |

|     |                | -continued |
| --- | -------------- | ---------- |
|     | Purified water | 75.75      |
| (C) | Ethanol        | 1.0        |
|     | Perfume        | 0.1        |

A skin cream was prepared with use of the above formula. Part (A) and part (B) were heated at 80° C. and at 81° to 82° C., respectively, to dissolve the respective components homogeneously. After the respective components were dissolved, part (B) was added to part (A) while stirring the latter, to obtain an emulsion. After completion of the addition, the stirring and cooling were continued, and part (C) was added at a temperature of from 60° to 65° C. When the temperature reached 30° C., the stirring was stopped, and after left to stand still, the product was filled into a container. The product thus obtained was stored in a constant temperature chamber at 40° C. for 3 months. The product did not undergo any change in its appearance or its feeling when applied to the skin, and it was satisfactory when used as a cosmetic.

EXAMPLE 2 (MEDICINAL SKIN CREAM)

| (A) | Egg oil                                  | 0.5% by weight |
|-----|------------------------------------------|----------------|
|     | 2-Octyldodecyl oleate                    | 2.0            |
|     | Liquid paraffin (#70)                    | 5.0            |
|     | Glyceryl monostearate                    | 7.0            |
|     | White petrolatum                         | 10.0           |
|     | Stearic acid                             | 8.0            |
|     | Polyoxyethylene (45) monostearate        | 1.2            |
|     | DL-α-tocopherol                          | 0.02           |
|     | Allantoin                                | 0.01           |
|     | Butyl p-hydroxybenzoate                  | 0.1            |
|     | Dibutylhydroxytoluene                    | 0.05           |
| (B) | Methyl p-hydroxybenzoate                 | 0.1            |
|     | Potassium hydroxide (10% aqueous solution) | 5.0          |
|     | Purified water                           | 60.92          |
| (C) | Perfume                                  | 0.1            |

A medicinal skin cream was prepared with use of the above formulations in a manner similar to Example 1. The product was stored in a constant temperature chamber at 40° C. for 3 months. The quality was stable without any change and quite satisfactory as a medicinal cream.

EXAMPLE 3 (SKIN LOTION)

| (A) | Soybean phospholipid              | 6.0% by weight |
|-----|-----------------------------------|----------------|
|     | 2-Octyldodecyl myristate          | 2.0            |
|     | Polyoxyethylene (40) monostearate | 1.0            |
|     | Cetyl alcohol                     | 1.3            |
|     | Liquid paraffin (#70)             | 1.0            |
|     | Butyl p-hydroxybenzoate           | 0.1            |
|     | Dibutylhydroxytoluene             | 0.05           |
| (B) | Sorbitol solution (70% aqueous solution) | 7.0     |

|     |                                         | -continued |
|-----|-----------------------------------------|------------|
|     | Hydroxypropyl cellulose (1% aqueous solution) | 30.0  |
|     | Methyl p-hydroxybenzoate                | 0.1        |
|     | Purified water                          | 44.35      |
| (C) | Ethanol                                 | 7.0        |
|     | Perfume                                 | 0.1        |

A skin lotion was prepared with use of the above formula in a manner similar to Example 1. This product has the desired effects.

Having now fully described the invention, it will be apparent to one of ordinary skill in the art that many changes and modifications can be made thereto without departing from the spirit of the invention as set forth herein.

What is claimed as new and intended to be covered by Letters Patent is:

1. A skin care base material composition for application to the external surface of skin which consists essentially of (A) a phospholipid, (B) an ester of a 8-26 carbon fatty acid with a 8-22 carbon primary aliphatic alcohol and (C) a polyoxyethylene 8-26 carbon fatty acid monoester containing 20-60 ethylene oxide units in weight amounts of 0.05-20 percent by weight of (A) 0.02-10 percent by weight of (B) and 0.01-5 percent by weight of (C), based on the weight of the entire composition and the balance of the composition comprises a cosmetic carrier.

2. The skin care base material of claim 1, wherein the phospholipid is soybean phospholipid.

3. The skin care base material of claim 1, wherein the ester of a fatty acid (B) is octyldodecyl myristate.

4. The skin care base material of claim 1, wherein the ester of a fatty acid (B) is octyldodecyl oleate.

5. The skin care base material of claim 1, wherein the polyoxyethylene fatty acid ester is polyoxyethylene monooleate.

6. The skin care base material of claim 1, wherein the polyoxyethylene fatty acid ester (C) is polyoxyethylene monostearate.

7. The skin care base material of claim 1 wherein the ester (B) is an ester of a branched primary aliphatic alcohol.

8. The skin care base material of claim 1 wherein the phospholipid (A) contains 10-40% phosphatidylcholine.

9. The skin care base material of claim 7 wherein the phospholipid (A) contains 10 to 40% of phosphatidylcholine.

10. The skin care base material of claim 9 wherein the phospholipid (A) is soybean phospholipid or egg phospholipid, wherein the ester of a fatty acid (B) is octyldodecyl myristate, octyldodecyl oleate or hexyldecyl dimethyloctanoate, and the polyoxyethylene fatty acid monoester (C) is polyoxyethylene monooleate or polyoxyethylene monostearate.

* * * * *